United States Patent [19]

Banks et al.

[11] Patent Number: 5,620,874
[45] Date of Patent: Apr. 15, 1997

[54] PROCESS FOR PRODUCING PARASITICIDAL MILBEMYCIN DERIVATIVES BY CULTURING STREPTOMYCES

[75] Inventors: Rhona M. Banks, Tadworth; Geoffrey H. Baker; Roderick J. Dorgan, both of Epsom; Mark E. Poulton, Tadworth, all of England

[73] Assignee: Pfizer Inc., New York, N.Y.

[21] Appl. No.: 457,809

[22] Filed: Jun. 1, 1995

Related U.S. Application Data

[63] Continuation of Ser. No. 303,889, Sep. 9, 1994, abandoned, which is a continuation of Ser. No. 108,790, Aug. 18, 1993, abandoned, which is a continuation of Ser. No. 496,112, Mar. 19, 1990, abandoned, which is a continuation of Ser. No. 76,274, Jul. 22, 1987, abandoned.

[30] Foreign Application Priority Data

| Jul. 24, 1986 | [GB] | United Kingdom | 8618096 |
| Jul. 29, 1986 | [GB] | United Kingdom | 8618473 |
| Aug. 22, 1986 | [GB] | United Kingdom | 8620424 |
| Sep. 11, 1986 | [GB] | United Kingdom | 8621873 |
| Sep. 11, 1986 | [GB] | United Kingdom | 8621874 |
| Oct. 25, 1986 | [GB] | United Kingdom | 8625596 |
| Jan. 13, 1987 | [GB] | United Kingdom | 8700673 |

[51] Int. Cl.$^6$ .................................................. C12B 17/79
[52] U.S. Cl. ........................... 435/119; 435/134; 435/76; 435/253.5
[58] Field of Search .................... 435/119, 124, 435/76, 253.5

[56] References Cited

U.S. PATENT DOCUMENTS

| 4,093,629 | 6/1978 | Fisher | 514/30 |
| 4,144,352 | 3/1979 | Putter | 514/450 |
| 4,310,519 | 1/1982 | Albers-Schonberg | 435/76 |

FOREIGN PATENT DOCUMENTS

| 0074758 | 3/1983 | European Pat. Off. | 549/264 |
| 0170006 | 2/1986 | European Pat. Off. | 435/119 |
| 0274871 | 6/1988 | European Pat. Off. | |
| 1390336 | 4/1975 | United Kingdom | 435/119 |
| 2166436 | 5/1986 | United Kingdom | 435/119 |
| 2176182 | 12/1986 | United Kingdom | |

OTHER PUBLICATIONS

*J. Antibiotics*, 29 (3), pp. 76–14–76–16 (1976).
*J. Antibiotics*, 29(3), pp. 76–35–76–42 (1976).

*Primary Examiner*—Irene Marx
*Attorney, Agent, or Firm*—Peter C. Richardson; Paul H. Ginsburg; Alan L. Koller

[57] ABSTRACT

Compounds of formula (I):

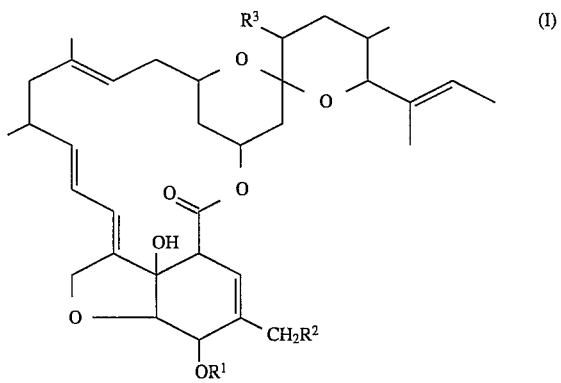

wherein $R^1$ is hydrogen or methyl, $R^2$ is hydrogen or (E)-2-methyl 2-butenoyloxy, and $R^3$ is hydrogen or hydroxy, with the proviso that when $R^3$ is hydrogen, $R^1$ and $R^2$ are both hydrogen, and when $R^2$ is (E)-2-methyl 2-butenoyloxy, $R^1$ is methyl; the compound of formula (II):

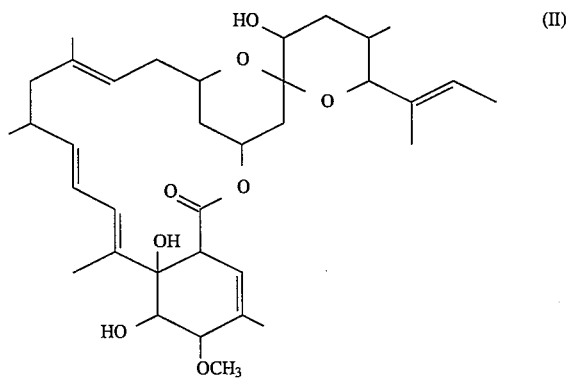

and the compound of formula (III):

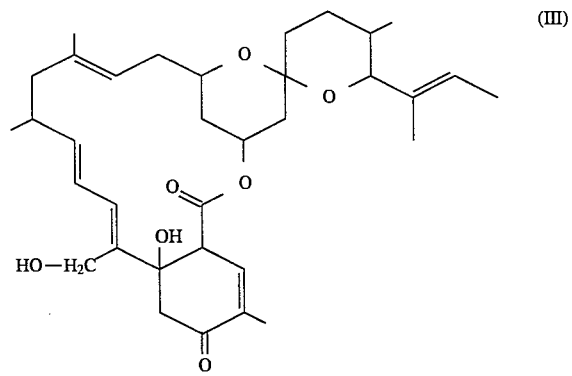

are obtainable by the fermentation of Streptomyces E225 NCIB 12310 or Streptomyces E225B NCIB 12509. The compounds have antihelminthic utility.

5 Claims, No Drawings

PROCESS FOR PRODUCING PARASITICIDAL MILBEMYCIN DERIVATIVES BY CULTURING STREPTOMYCES

This application is a continuation of application Ser. No. 08/303,889, filed Sep. 9, 1994, now abandoned, which is a continuation of application Ser. No. 08/108,790, filed Aug. 18th, 1993, now abandoned, which is a continuation of application Ser. No. 07/496,112, filed Mar. 19, 1990, now abandoned, which is a continuation of application Ser. No. 07/076,274, filed Jul. 22, 1987, now abandoned.

The present invention relates to novel anthelmintically active materials obtainable from a microorganism, to processes for their production, to pharmaceutical formulations containing them, and to their use in human or veterinary medicine.

A large number of microorganisms have been isolated, in particular from soil samples, and certain of those microorganisms have been found to produce various metabolites, which can be isolated and some of which have useful biological activity. One group of such metabolites is the milbemycins, which have been prepared by the cultivation of microorganisms of the genus Streptomyces and are described in inter alia GB-A-1,390,336, J. Antibiotics 29 (3), 76–14 to 76–16 and 29 (6), 76–35 to 76–42, U.S. Pat. No. 4,144,352, and GB-A-2 056 986.

The α series of milbemycins include compounds of formula A:

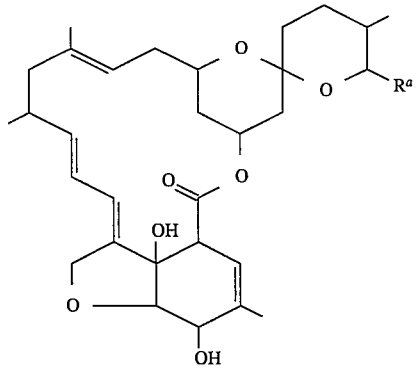

wherein $R^a$ is methyl, ethyl or isopropyl. In U.S. Pat. No. 4,144,352 it was disclosed that these and related compounds have anthelmintic activity.

Various milbemycin derivatives are disclosed in U.S. Pat. Nos. 4,093,629 and 4,134,973.

EP-A-0 170 006 and GB-A-2 166 436 disclose six further compounds of formula B:

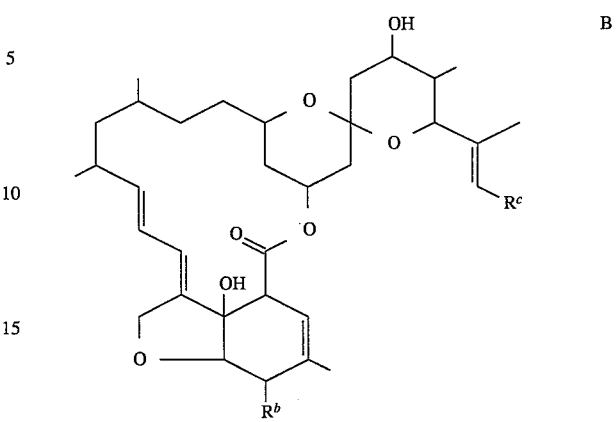

wherein $R^b$ is hydroxy or methoxy and $R^c$ is methyl, ethyl or isopropyl. These compounds were also prepared by the cultivation of Streptomyces microorganisms, and are stated to have anthelmintic activity.

We have now discovered a new group of compounds obtainable by the cultivation of a streptomyces microorganism. These compounds have anthelmintic properties, and therefore are of use in the treatment of helminthiasis in humans and animals.

The present invention accordingly provides compounds of formula (I):

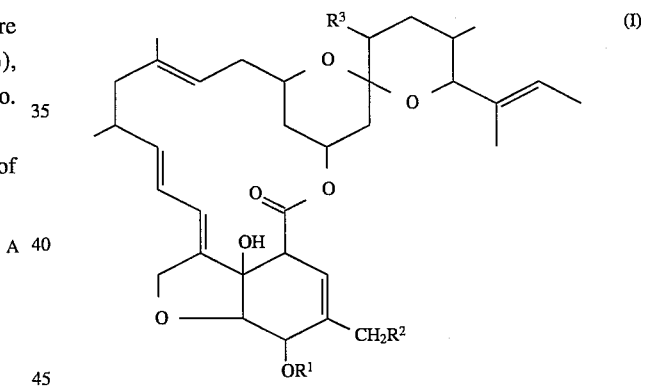

wherein $R^1$ is hydrogen or methyl, $R^2$ is hydrogen or (E)-2-methyl 2-butenoyloxy and $R^3$ is hydrogen or hydroxy, with the proviso that when $R_3$ is hydrogen, $R^1$ and $R^2$ are both hydrogen, and when $R^2$ is (E)–2-methyl 2-butenoyloxy, $R^1$ is methyl.

Compounds of formula (I) are set out in Table I below:

TABLE I

| Compound | $R^1$ | $R^2$ | $R^3$ |
|---|---|---|---|
| VM44857 | H | H | H |
| VM44864 | $CH_3$ | H | OH |
| VM44865 | $CH_3$ | ![structure] | OH |
| VM44866 | H | H | OH |

A further aspect of the invention provides VM 44867, which is the compound of formula (II):

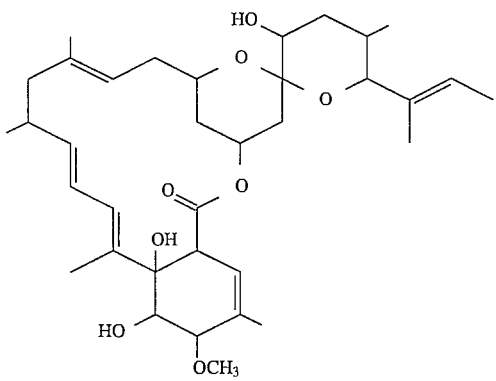

A still further aspect of the invention provides VM 44868, which is the compound of formula (III):

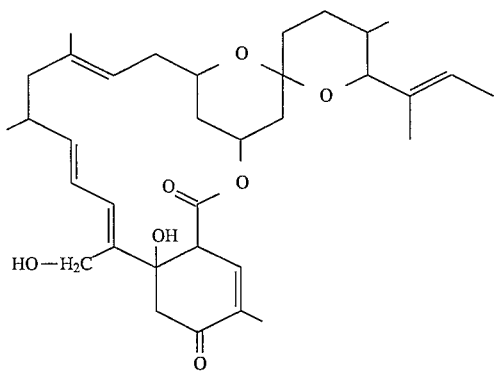

Characterizing data for the compounds of the invention are set out hereinbelow in the Examples.

The present invention also provides a process for the production of a compound of the invention or a derivative thereof, which comprises cultivating a producing microorganism, and subsequently isolating the compound or derivative thereof from the culture.

The present invention furthermore provides a process for the preparation of a compound of the invention or derivative thereof, which comprises chromatographically separating the compound or derivative thereof from a solution thereof in admixture with other substances into a fraction comprising the compound or derivative thereof and other fractions. The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the cultivation process according to the invention include bacterial strains belonging to the genus Streptomyces that are capable of elaborating compounds according to the invention. It has further been found that examples of such strains include Streptomyces E225, which has been isolated from soil, and also mutants and natural variants thereof such as Streptomyces E225B.

The term 'mutant' as used herein includes any mutant strain which arises spontaneously or through the effect of an external agent whether that agent is applied deliberately or otherwise. Suitable methods of producing mutant strains include those outlined by H.I.Adler in 'Techniques for the Development of Microorganisms' in "Radiation and Radioisotopes for Industrial Microorganisms", Proceedings of a Symposium, Vienna, 1973, page 241, International Atomic Engergy Authority, and these include:

(i) Ionizing radiation (e.g. X-rays and γ-rays), u.v. light, u.v. light plus a photosensitizing agent (e.g. 8-methoxypsoralen), nitrous acid, hydroxylamine, pyrimidine base analogues (e.g. 5-bromouracil), acridines, alkylating agents (e.g. mustard gas, ethyl-methane sulphonate), hydrogen peroxide, phenols, formaldehyde, nitrosoguanidine, heat, and (ii) Genetic techniques, including, for example, recombination, transformation, transduction, lysogenisation, lysogenic conversion, protoplast fusion, and selective techniques for spontaneous mutants.

Streptomyces E225 and Streptomyces E225B are believed to comprise a previously unreported strain in the genus Streptomyces and therefore form part of the present invention, more particularly in biologically pure form. They have been deposited in the National Collection of Industrial and Marine Bacteria, Aberdeen, Scotland, the deposits (NCIB 12310 and 12509; filing dates 23rd Jul., 1986 and 20th. Jul. 1987) being made under the terms of the Budapest Treaty on the International Recognition of the Deposit of Micro-organisms for the Purposes of Patent Procedure.

The characteristics of Streptomyces E225 were as follows:

After being grown on starch casein agar medium for 7 to 14 days at 27° C., Streptomyces E225 had produced a yellow-brown vegetative mycelium in which the hyphae did not fragment into coccoid or bacillary elements, and a yellow or white aerial mycelium which turned grey as the culture aged. The culture also produced a yellow soluble pigment and some colonies were observed to exude yellow droplets; The sporophores were arranged singly or in pairs along straight or flexuous main aerial hyphae, with no evidence of true verticillate branching, and terminated in spirals of 4 to 6 turns. Some sporophores presented a warty appearance, whilst older cultures developed moist black areas where spores had massed together.

Streptomyces E225 was non-sporulating on a yeast-malt agar medium. The fermentation medium for cultivating the producing organism suitably contains sources of assimilable carbon and assimilable nitrogen together with inorganic salts. Suitable sources of nitrogen include yeast extract, soybean flour, meat extract, cottonseed flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium), alkaline earth metal ions (for example, calcium and magnesium), halogen ions (for example, chloride), and trace elements (for example, iron, zinc, copper, manganese and cobalt).

The cultivation may suitably be effected at a temperature of about 20° to 35° C., advantageously 27° to 28° C., and the culture may suitably be harvested after 2 to 35 days, advantageously about 5 to 20 days, after the initiation of fermentation in order to given an optimum yield of the desired compound of the invention.

The desired compound or derivative thereof may then be isolated from the culture medium and worked up and purified using conventional techniques.

The desired product may be obtained from either the mycelial growth or from the culture filtrate. It may therefore be convenient for the first isolation step to involve the separation of solid material from the fermentation broth by, for example, filtration or centrifugation, to give a clarified culture filtrate and solid material. Alternatively, the fermentation broth can be extracted directly.

It may be convenient to include an organic solvent extraction step in the isolation or purification procedure, suitably using a solvent such as acetone or hexane.

Further isolation of the desired compound may conveniently be effected by chromatographic techniques. The extract may contain additional substances, and therefore chromatographic separation may-result in a plurality of fractions, of which the desired fraction or fractions is or are the fraction(s) comprising the desired compound or a derivative thereof.

The desired fraction(s) may readily be identified in a routine manner by testing for anthelmintic activity and/or by monitoring each fraction chromatographically. The desired fraction(s) is/are that/those identified by such procedures as containing the desired compound or a derivative thereof.

If necessary, repeated chromatographic separation may be carried out in a routine manner. At each stage of the separation procedure, the fractions containing the desired compound or a derivative thereof may be combined and then subjected to further purification steps. In the initial separation steps, it may be convenient to identify the desired fractions merely as those having anthelmintic activity and to combine all such fractions. In later stages of the separation, it may be necessary to identify the desired fraction or fractions more precisely in order to separate the desired compound or a derivative thereof from any other substances that maybe present. Separation may advantageously be continued in order to give one or more fractions consisting essentially of the desired compound or a derivative thereof.

The expression 'fraction consisting essentially of the desired compound or a derivative thereof' means a fraction containing the desired compound or a derivative thereof as the sole component present in that fraction, or as the major component (whether other components are active or are inactive impurities) present in that fraction. The expression 'major component' means the component that is present in the greatest amount relative to other individual components (exclusive of solvent). Suitably, the major component is present in an amount greater than the sum of the amounts of all other components (excluding solvent). More suitably, the major component is present in an amount of at least 60% advantageously at least 70% preferably at least 80%, especially from 90% to 100%, by weight, relative to the total amount of active material, or relative to the total amount of material whether active or inactive (exclusive of solvent), as the case may be, present in the fraction. Typically, the compounds of the invention are produced in admixture with one another, so that fractions may be obtained which consist essentially of a mixture of two or more compounds of the invention.

It has been found convenient to carry out chromatographic separation on silica gel (using, for example, a silica 60 column). Two or more chromatographic separation steps may be carried out successively. Elution of the chromatographic columns may conveniently be effected using organic solvents, either alone or in admixture with one another, e.g. hexane/acetone, diethylether/petroleum ether, or methanol/chloroform.

The compound or mixture of compounds according to the invention is suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for; example, be used in the preparation of a more pure form of the same compound or of a related compound (for example a corresponding derivative) suitable for pharmaceutical use.

The compounds of the invention have parasiticidal properties, for example against nematodes such as *Trichostrongylus colubriformis,* and are useful for the treatment of helminthiasis in animals such as mammals, including humans and domesticated animals (including farm animals).

Accordingly the present invention also provides a compound according :to the invention, for use in the treatment of the human or animal body, especially for treating endo- and ectoparasitic infestations and particularly for treating helminthiasis of domestic and farm animals.

The term helminthiasis encompasses those diseases of man and animals caused by infestation with parasitic worms such as Strongyles, Ascarids, hookworms lungworms, filarial worms and whipworms. The compound may also be used against nematodes occurring in the soil or parasitic to plants.

The compounds of the invention are also active against Arthropods. The phylum Arthropoda comprises insects— such as biting flies, lice, bugs, beetles and fleas— and arachnids— such as mites and ticks.

Thus, a broad aspect of the invention provides a method of eradicating arthropod or nematode infestations, which method comprises applying a compound according to the invention or a derivative thereof to the arthropods or nematodes or to their environment.

The present invention thus provides a pesticidal composition comprising a compound according to the invention or a derivative thereof together with a suitable carrier or excipient, such as an aerosol formulation.

The present invention also provides a pharmaceutical or veterinary composition comprising a compound according to the invention or a pharmaceutically acceptable derivative thereof together with a pharmaceutically or veterinarily acceptable carrier or excipient.

The present invention also provides a method of treatment or prophylaxis of endo- and ectoparasitic infestations, especially helminthiasis, of animals, especially humans and domesticated mammals, which comprises administering an effective non-toxic amount of a compound according to the invention or a pharmaceutically acceptable derivative thereof, or a composition according to the invention, to a patient in need thereof.

The composition according to the invention may be formulated for administration in any convenient way for use in human or veterinary medicine, by analogy with other anthelmintics.

In suitable formulations the drug may be administered to animals orally (as a paste, drench, bolus, capsule or tablet), parenterally, percutaneously, as a food additive (eg granules, pellets or powder), or may be prepared as an aerosol spray formulation.

The compounds of the invention may be formulated as a mixture with each other and/or with other anthelmintics, insecticides, acaricides or other pharmacologically active substances.

Suitably the composition consists of sufficient material to provide a dose of from 0.01 to 100 mg of active ingredient per kg of animal body weight per dose, more suitably 0.1 to 10 mg/kg per dose.

A composition according to the invention may suitably contain from 0.1% by weight, preferably from 1.0 to 60% by weight, of the compound according to the invention (based on the total weight of the composition), depending on the method of administration.

In certain circumstances the crude fermentation broth may be administered, for example by incorporating the freeze-dried fermentation broth into the feed of the animal.

It will be appreciated that, in some cases, it will be advisable to repeat the dosing of the infected or potentially infected human or animal with the compound of the invention according to conventional dosage regimes used with anthelmintics.

The following Examples illustrate the invention.

EXAMPLE 1

Production and isolation of VM 44857 a) Fermentation

Streptomyces E225 was grown at 27° C. on a solid agar plate of starch casein. A portion of growth taken from the agar plate was used to inoculate the seed medium (50 ml) contained in a 250 ml Erlenmeyer flask.

The seed stage was incubated at 27° C. on a gyratory shaker at 240 r.p.m. for 48 hours. The seed medium had the following composition:

| Constituent | Amount (g/l) |
| --- | --- |
| Soybean flour | 10.0 |
| Glycerol | 20.0 |
| Maltose | 2.0 |
| Trace element mix | 10 ml stock/liter |
| Deionised water | to 1 liter |

(The soybean flour was Arkasoy 50 as supplied by British Arkady Co. Ltd., Old Trafford, Manchester U.K.)

The trace element mix comprised:

| Constituent | Amount (g/l) |
| --- | --- |
| $CaCl_2\ 2H_2O$ | 10.0 |
| $MgCl_2\ 6H_2O$ | 10.0 |
| NaCl | 10.0 |
| $FeCl_3$ | 3.0 |
| Zncl | 0.5 |
| $CuCl_2\ 2H_2O$ | 0.5 |
| $MnSO_4\ 4H_2O$ | 0.5 |
| $CoCl_2\ 6H_2O$ | 0.5 |

The medium was adjusted to pH 6.5 before sterilisation.

Portions (2 ml)of the seed stage were used to inoculate the fermentation medium (50 ml) contained in 250 ml Erlenmeyer flasks. The fermentation medium contained:

| Constituent | Amount (g/l) |
| --- | --- |
| Soluble starch | 10 |
| Casein (Sigma C5890) | 1.0 |
| Dipotassium hydrogen phosphate | 0.5 |
| Magnesium sulphate | 0.5 |

(Sigma C5890 was supplied by Sigma Chemical Co. Ltd., Poole, Dorset, England "Sigma" is a Trade Mark).

The medium was adjusted to pH 7.0 before sterilisation.

The fermentation was incubated on a gyratory shaker at 240 r.p.m at 27 C. for 19 days.

Fermentation samples were assayed by testing for in vitro anthelmintic activity for example against Haemonchus contortus $L_3$ larvae.

After 19 days the whole broth from 100 fermentation flasks was combined and centrifuged and the supernatant discarded.

b) Isolation of Substantially Pure VM 44857

The cell pellet obtained in (a) was slurried with water (0.75 1), mixed with acetone (1.5 1) and allowed to stand for 48 hours at 4° C. The slurry was then filtered (Hyflo supercel, BDH Chemicals Ltd., Eastleigh, Hampshire, England "Hyflo" is a Trade Mark), the residue washed with acetone (3×250 ml) and the combined filtrates were evaporated to remove the acetone.

The aqueous residue (600 ml) was mixed with methanol (500 ml) and the whole extracted with hexane (3×500 ml). The combined hexane extracts were evaporated, the residue (412 mg) was dissolved in methanol (41.2 ml) and allowed to stand at −20° C. overnight. After filtration to remove the precipitate which had formed, the filtrate was evaporated and the residue (295 mg) chromatographed on silica (75 g) eluting with 0 to 20% acetone in hexane. Fractions containing VM 44857, VM 44864 and VM 44866, detected by t.l.c., were collected. The combined VM 44857 fractions were evaporated to give the product (25 mg) as an oil. Final purification was effected by preparative thin layer chromatography using silica gel taper plates (ex Analtech, Anachem House, Luton, Bedfordshire, England) eluted with diethyl ether/petroleum ether 70/30 to give VM 44857 (6 mg) $R_f$ value in t.l.c. on a silica gel support using a diethyl ether/petroleum ether (70:30) solvent system=0.3.

Characterizing data $\lambda$max ($CH_3OH$) 244 nm; m/z (FAB $Na^+$/Noba) (relative intensity) 591 (100%) $[MNa]^+$; $\delta_C$ ($CD_2Cl_2$) 173.2, 142.2, 139,5, 137.5, 136.6 134.6, 123.3, 123.0, 120.8, 119.7, 117.7, 97.4, 82.0, 79.8, 7 9.0, 68.4, 68.1, 67.3, 67.3, 48.1, 45.4, 40.8, 36.1, 35. 7, 35.3, 34.3, 31.2, 27.2, 21.8, 19.2, 17.1, 14.9, 12. 5, and 10.4 ppm. It has a retention time of 17.4 minutes when subjected to hplc under the following conditions: an Ultrasphere ODS 5μm column (Altex 250×4.6 mm) is eluted with methanol/water (90:10) at a flow rate of 1 ml/minute and monitored by UV absorption at 246 nm. $[\alpha]_D 25$ (acetone)+1110° (C=0.25).

EXAMPLE 2

Production and isolation of VM 44864

The procedure described in Example 1 additionally yielded VM 44864 (4mg) $R_f$ value in t.l.c. on a silica gel support using a diethyl ether/petroleum ether (80:20) solvent system=0.4.

Characterising data $\lambda$max ($CH_3OH$) 244 nm and 237 nm; m/z (FAB $Na^+$/Noba) (relative intensity) 621 (100%) $[MNa]^+$; $[\alpha]_D 25$ (acetone)+96.8 (c=0.25); $\delta_C$ ($CDCl_3$) 173.8, 142.3, 139.8, 137.2, 135.9, 134.1, 123.6, 123.5, 120.5, 119.5, 118.5, 98.6, 81.9, 80.3, 77.5, 76.9, 71.5, 68.6, 68.2, 68.0, 57.7, 48.5, 45.6, 36.6, 36.4, 36.3, 35.9, 34.6, 32.1, 22.3, 19.9, 17.5, 15,6, 13.1 and 10.9 ppm. It has a retention time of 7.0 minutes when subjected to hplc under the conditions described in Example 1.

EXAMPLE 3

Production and isolation of VM 44866

The procedure described in Example 1 additionally yielded VM 44866 (3mg) $R_f$ value in t.l.c. on a silica gel support using a diethyl ether/petroleum ether (80:20) solvent system=0.25.

Characterising data $\lambda_{max}$ ($CH_3OH$) 244 nm and 236 nm; m/z (FAB $Na^+$/Noba) (relative intensity) 607 (100%) $[MNa]^+$; $[\alpha]_D 25$ (acetone)+ 81.9 (c=0.16); $\delta^{13}C$ ($CDCl_3$) 173.7, 142.7, 139.5, 137.8, 137.2, 134.1, 123.6, 123.4, 120.6, 120.2, 118.0, 98.8, 81.9, 80.1, 79.1, 71.6, 68.6, 68.4., 68.0, 67.7, 48.5, 45.7, 36.9, 36.5, 36.4, 36.0, 34.6, 32.1, 22.3, 19.9, 17.5, 15.5, 13.1, 10.9 ppm. It has a retention time of 5.8 minutes when subjected to hplc under the conditions described in Example 1.

EXAMPLE 4

Production and isolation Of VM 44865.

Portions (2 ml) of the seed stage obtained as described in Example 1 were used to inoculate the fermentation medium (50 ml) contained in 250 ml Erlenmeyer flasks. The fermentation medium contained:

| Constituent | Amount (g/l) |
| --- | --- |
| Casein hydrolysate | 2.0 |
| Glucose | 20.0 |
| Soluble starch | 20.0 |
| Casein (Sigma C5890) | 2.0 |
| Dipotassium hydrogen phosphate | 0.5 |
| Magnesium sulphate | 0.5 |
| Calcium carbonate | 5.0 |
| Trace element mix as in Example 1 | 10 ml stock/liter |

(Sigma C5890 was supplied by Sigma Chemical Co. Ltd., Poole, Dorset, England "Sigma" is a Trade Mark).

The medium was adjusted to pH 7.0 before sterilisation.

The fermentation was incubated on a gyratory shaker at 240 r.p.m at 27° C. for 13 days.

Fermentation samples were assayed by testing for in vitro anthelmintic activity for example against *Haemonchus contortus* $L_3$ larvae.

After 13 days the whole broth from 100 fermentation flasks was combined and centrifuged and the supernatant discarded.

Isolation of Substantially Pure VM 44865

The cell pellet obtained in (a) was slurried with water (0.75 l), mixed with acetone (1.0 l) stirred for 30 min and filtered. The acetone extraction was repeated three times, and the combined filtrates evaporated to remove the acetone.

The aqueous residue (600 ml) was extracted with chloroform (4×500 ml). The combined chloroform extracts were dried (MgSO$_4$) and evaporated. The residue (6 g) was chromatographed on silica (100 g) and gradient eluted with 0 to 100% ether in hexane. Fractions containing VM 44865, detected by t.l.c., were combined and evaporated to give the crude product (520 mg) as an oil. Final purification was effected by further column chromatography using silica (75 g) eluted with 0 to 100% ether in hexane to give VM 44865 (11 mg) $R_f$ value in t.l.c. on a silica gel support using a dichloromethane/methanol (95:5) solvent system =0.4.

Characterizing data $\lambda_{max}$ (CH$_3$OH) 244 nm; m/z (FAB Na$^+$/Noba) (relative intensity) 719 (100%) [MNa]$^+$; $\delta^{13}$C (CDCl$_3$) $\delta^{13}$C 173.3, 167.5, 142.6, 139.4, 237.6, 137.2, 134.9, 134.1, 128.4, 123.6, 123.4, 121.0, 220.5, 119.8, 98.8, 81.9, 80.4, 77.3, 74.2, 71.5, 68.9, 68.3, 68.0, 64.3, 57.8, 48.5 45.5, 36.9, 36.4, 36.3, 35.9, 34.6, 32.1, 22.3, 17.5 15.6, 14.4, 13.1, 12.1, 11.0 ppm. It has a retention time of 8.0 minutes When subjected to hplc under the conditions described in Example 1.

EXAMPLE 5

Production and isolation of VM 44867
(a) Fermentation

Streptomyces E225 was grown at 27° C. on an agar plate of starch casein medium. A portion of the culture was used to inoculate six 500 ml Erlenmeyer flasks, each containing 100 ml of sterilised seed medium. The flasks were incubated at 27° C. on a gyratory shaker at 240 rpm for 48 hours.

The seed medium was made up as described in Example 1.

The flask contents were used to inoculate 15 l seed medium in a 20 l stainless steel fermenter. The medium was of the same composition except that tap water was used in place of deionised water. Prior to sterilisation the medium was pH 6.3 and was not adjusted. The seed stage culture was agitated at 200 rpm. and air was supplied at a rate of 15 l/mm. Temperature was controlled at 28° C. Polypropylene glycol P2000(supplied by KWR Chemicals Ltd, Eleanor House, 33–35 Eleanor Cross, Waltham Cross, Herts.) was added automatically to control foaming. Incubation was continued for 48 hours at which time 4 l of the culture was used to inoculate 100 l production medium contained in a 150 l stainless steel fermenter. The production medium had the following composition:

| Constituent | Amount (g/l) |
| --- | --- |
| Potato Starch | 20 |
| Casein | 2 |
| Glucose | 20 |
| Casein hydrolysate | 2 |
| K$_2$HPO$_4$ | 0.5 |
| MgSO$_4$ | 0.5 |
| CaCO$_3$ | 0.5 |
| Trace element mix as in Example 1 | 10 ml/l |
| Tap water | to 1 l |

Prior to sterilisation the medium was pH 7.0

Potato starch and casein were supplied by British Drug Houses Ltd, Broom Road, Parkstone, Poole, Dorset. U.K.

Casein hydrolysate was supplied by Oxoid Ltd, Wade Road, Basingstoke, Hampshire U.K.

The production stage culture was agitated at 160 rpm and air was supplied at a rate of 50 l/min. Temperature was maintained at 28° C. Polypropylene glycol P2000 was added automatically to control foaming. The fermentation was harvested after 15 days and centrifuged to recover the mycelial mass.

(b) Isolation of VM44867

The mycelial mass obtained in (a) was extracted with acetone (2×40 l) and concentrated to remove the acetone. The residue (14 l) was then extracted with dichloromethane (2×6 l), the combined extracts dried (MgSO$_4$) and evaporated to an oil (40 g).

The residue was chromatographed on silica and eluted sequentially with 0 to 60% diethyl ether/hexane. Fractions containing VM 44867, as detected by hplc, were combined and evaporated to give the semi-purified product as an oil (66 mg). Final purification was effected by preparative thin layer chromatography using silica gel taper plates (ex Analtech, Anachem House, Luton, Bedfordshire, England) eluted with methanol/dichloromethane 3:97 to give substantially pure VM 44867 (4.7 mg) $R_f$ value in t.l.c. on a silica gel support using a methanol/dichloromethane (3:97) solvent system=0.3.

Characterizing data $\lambda$max (CH$_3$OH) 244 nm; M/$_z$ (FAB Na$^+$/Noba) (relative intensity) 623 (100%) [MNa]$^+$. E.I. observed mass 600.3659 C$_{35}$H$_{52}$O$_8$ requires 600.3662. $\delta^{13}$C (CDCl$_3$) 174.7, 140.4, 137.4, 1361, 134.7, 134.0, 125.5, 124.7, 123.7, 120.6, 118.S, 98.8. 81.8, 79.8, 77*, 71.6, 69.5, 68.1, 68.0, 57.4, 48.6, 44.4, 36.9, 36.2, 36.2, 35.5, 34.5, 32.1, 21.4, 19.3, 17.5, 16.1, 13.8, 13.1 and 10.9 ppm. It has a retention time of 9.5 minutes when subjected to hplc under the conditions described in Example 1. [$\alpha$]$_D$25=+51° (acetone, c=0.21).

* this signal was obscured by the solvent signals.

EXAMPLE 6

Production and isolation of VM44868
(a) Fermentation

Streptomyces E225 was grown at 27° C. on an agar plate of starch casein medium. A portion of the culture was used to inoculate five 500 ml Erlenmeyer flasks, each containing 100 ml of sterilised seed medium. The flasks were incubated at 28° C. on a gyratory shaker at 240 rpm for 72 hours.

The seed medium had the following composition:

| Constituent | Amount (g/l) |
| --- | --- |
| Oxoid Special Peptone* | 2.5 |
| Oxoid Lab Lemco* | 2.5 |
| Oxoid Tryptone* | 2.5 |
| Oxoid Neutralised Soya Peptone* | 2.5 |
| Soluble starch | 2.5 |
| Glucose monohydrate | 2.5 |
| Oxoid Malt Extract* | 2.5 |
| Glycerol | 2.5 |
| Trace Element Mix as in Example 1 | 10 ml stock/liter |
| Deionised water | to 1 liter |
| pH unadjusted. | |

*supplied by Oxoid Ltd, Wade Road, Basingstoke, Hampshire, UK.

The flask contents were used to inoculate 15 l seed medium in a 20 l stainless steel fermenter. The medium was of the same composition except that tap water was used in place of deionised water. The seed stage culture was agitated at 200 rpm. and air was supplied at a rate of 15 1/min. Temperature was controlled at 28° C. Polypropylene glycol P2000 (supplied by KWR Chemicals Ltd, Eleanor House, 33–35 Eleanor Cross, Waltham Cross, Herts.) was added automatically to control foaming. Incubation was continued for 48 hours at which time 4 l of the culture was used to inoculate each of two 150 l stainless steel fermenters containing 100 l of the following production medium.

Fermentation medium contained:

| Constituent | Amount (g/l) |
| --- | --- |
| Dextrin (1) | 25 |
| Black Treacle (2) | 1.5 |
| $CaCO_3$ | 1.25 |
| Glucose monohydrate | 2.5 |
| Arkasoy '50' (3) | 12.5 |
| P2000 | 1.0 |
| Tap Water | to 1 liter |
| pH adjusted to 6.5 | |

(1) 07005 Snowflake supplied by Corn Products (UK)Ltd Manchester.
(2) Supplied by Fowlers, Tate and Lyle Ltd., Croydon, Surrey, UK.
(3) Supplied by British Arkady Co. Ltd., Old Trafford, Manchester, UK.

One fermenter also contained 2.1% MOPS buffer together with 0.0125% $K_2HPO_4$. The other fermenter contained 0 05% $K_2HPO_4$.

Sterile air was provided to each vessel at 50 litres per minute and a pressure of 0.5 bar maintained in the head spaces. The cultures were stirred at 160 rpm initially, this was increased to prevent dissolved oxygen levels falling below 20% of saturation. Fermentation temperature was 28° C.

The vessel containing MOPS buffer maintained a constant pH of 7.0±0.1.

The vessel without added MOPS buffer was fitted with automatic addition of hydrochloric acid (10%) and sodium hydroxide solution (10%) to control pH in the range 6.8–7.2.

The fermentation broth was harvested from both fermenters after 168 hours, together with the solids which had accumulated above the liquid level around the walls of each vessel. The broth was centrifuged to recover the mycelial mass.

(b) Isolation of VM44868

The mycelial mass obtained in (a) was extracted three times with acetone (75 l, 30 l, and 25 l) and the combined extracts concentrated to remove the acetone. The residue (27 l) was extracted twice with dichloromethane (16 l and 8 l), the extracts were combined and evaporated to give an oil (220 g).

The residue was chromatographed on silica and eluted sequentially with 0 to 100% diethyl ether in hexane. Fractions containing VM 44868, as detected by hplc, were combined and evaporated to give the semi-purified product as an oil (900 mg). This was further purified by chromatography on silica eluted sequentially with 0 to 1% methanol in dichloromethane to give an oil (68 mg) .

Final purification was effected by preparative thin layer chromatography using silica gel taper plates (ex Analtech, Anachem House, Luton, Bedfordshire, England) eluted with diethylether/hexane (4:1) to give substantially pure VM 44868 (26 mg) $R_f$ value in t.l.c. on a silica gel support using a methanol/dichloromethane (7.5:92.5) solvent system= 0.45.

Characterising data $\lambda_{max}$ 237 nm($CH_3OH$); $M/_z$ (FAB $Na^+$/NOBA) (Relative intensity) 591 (100%) $[MNa]^+$, $[\alpha]_D 25+108°$ (c,0.29 acetone), $\delta^{13}C$ ($CDCl_3$) 196.5, 172.3, 144.8, 137.6, 136.8, 136.3, 136.0, 134.8, 130.4, 123.5, 123.0, 121.0, 97.6, 82.4, 78.0, 69.5, 67.4, 58,0, 49.9, 48.3, 48.0, 41.0, 36.6, 36.3, 35.6, 34.5, 31.5, 27.6, 21.7, 17.7, 16.0, 15.6, 13.0, 11.0, ppm. It has a retention time of 11.7 minutes when subjected to hplc under the conditions described in Example 1.

EXAMPLE 7

Biological Activity of VM 44857

Thirty 4-week-old Mongolian gerbils of mixed sex were each infected with 750 *Trichostrongylus colubriformis* infective larvae (sheep strain) by gavage. Twenty days after infection these animals were randomly allocated into six groups: two of four, three of five and one of seven. On the same day worm egg counts were carried out on pooled faecal samples from each group to confirm that the infections had established.

At 21 days post-infection the animals were treated as follows:

Group 1: VM 44857 at 1 mg/kg

Group 2: VM 44857 at 0.25 mg/kg

Group 3: VM 44857 at 0.1 mg/kg

Group 4:
VM 44857 at 0.025 mg/kg

Group 5: Albendazole at 0.25 mg/kg

Group 6: 50/50 mixture of DMSO/PEG 400 at 0.5 ml/gerbil

All treatments were administered orally by gavage.

VM 44857 was prepared as a 0.01% solution in a 50/50 mixture of DMSO and PEG 400. Dilutions of this solution were then prepared to provide the appropriate doses. The albendazole used was a dilution of proprietary Valbazen (Merck).

Three days after treatment worm egg counts were carried out on faecal samples from each group to determine the effect of treatment. All animals were then necropsied for recovery and enumeration of worms. The following method was adopted.

Each small-intestine was removed separately and slit open longitudinally with bowel scissors and jetted vigorously with water over a 150 micron test sieve. The washings retained on the sieve were concentrated and then examined for worms in a glass dish under a low power stereomicroscope. Assessment of activity was determined by comparison of worm counts of treated and untreated animals. The results are summarised in Table II.

TABLE II

| Treatment | Number of Worms Recovered | Mean | Activity % |
|---|---|---|---|
| VM44857 1 mg/kg | 0, 0, 1, 0, 0, | 0.2 | 99.4 |
| VM44857 0.25 mg/kg | 0, 0, 0, 0, | 0 | 100 |
| VM44857 0.1 mg/kg | 0, 0, 5, 0, | 1.25 | 96.4 |
| VM44857 0.025 mg/kg | 4, 7, 8, 33, 9, | 12.2 | 65 |
| Albendazole 0.25 mg/kg | 11, 1, 3, 9, 1, | 5 | 85.6 |
| Controls DMSO/PEG400 | 39 56 45 13 35 17 38 | 34.7 | — |

EXAMPLE 8

Biological Activity of VM 44864

Fifteen 4-week-old Mongolian gerbils of mixed sex were each infected with 750 *Trichostrongylus colubriformis* infective larvae (sheep strain) by gavage. Twenty days after infection these animals were randomly allocated into three groups of five. On the same day worm egg counts were carried out on pooled faecal samples from each group to confirm that the infections had established.

At 21 days post-infection the animals were treated as follows:

Group 1: VM 44864 at 1 mg/kg

Group 2: Ivermectin at 0.1 mg/kg

Group 3: 50/50 mixture of DMSO/PEG 400 at 0.5 ml/gerbil

All treatments were administered orally by gavage.

VM 44864 was prepared as a 0.01% solution in a 50/50 mixture of DMSO and PEG 400 and this solution was then diluted to provide the appropriate dose. The Ivermectin used was a dilution of proprietary Ivomec (Merck).

Three days after treatment worm egg counts were carried out on faecal samples from each group to determine the effect of treatment. All animals were then necropsied for recovery and enumeration of worms as described in Example 7. The results are summarised in Table III.

TABLE III

| Treatment | Number of Worms Recovered | Mean | Activity % |
|---|---|---|---|
| VM44864 1 mg/kg | 0, 1, 0, 0, 0, | 0.2 | 98.0 |
| Ivermectin 0.1 mg/kg | 1, 1, 0, 2, 0, | 0.8 | 91.0 |
| Controls DMSO/PEG400 | 3, 2, 5, 17, 18, | 9.0 | — |

We claim:

1. A process for the production of a compound of formula (I)

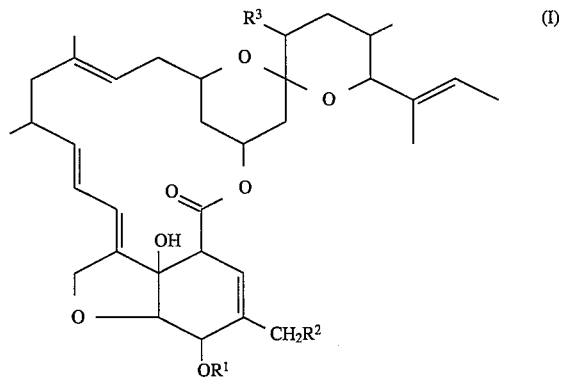

wherein $R^1$ is hydrogen or methyl, $R^2$ is hydrogen or E 2-methyl 2-butenoyloxy, and $R^3$ is hydrogen or hydroxy, with the proviso that when $R^3$ is hydrogen, $R^1$ and $R^2$ are both hydrogen, and when $R^2$ is E 2-methyl 2-butenoyloxy, $R^1$ is methyl, or a compound of formula (II)

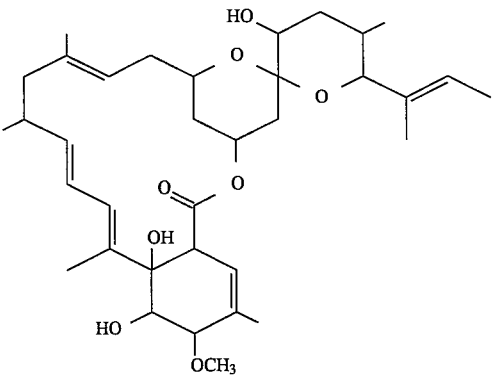

or a compound of formula (III)

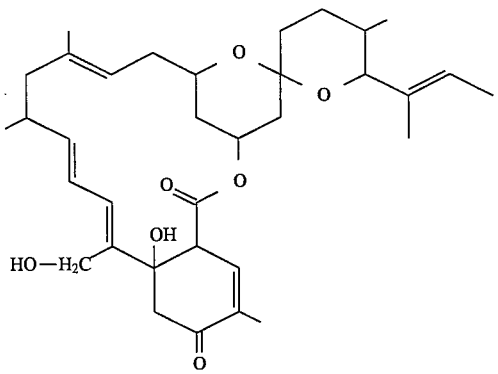

which process comprises cultivating a microorganism selected from the group consisting of Streptomyces E225, NCIB 12310, Streptomyces E225B, NCIB 12509, and any VM 44857, VM 44864, VM 44865, VM 44866, VM 44867, or VM 44868 producing mutant thereof, and recovering the desired compound of formula (I), (II), or (III).

2. The process according to claim 1, for the production of a compound of formula (I), wherein $R^1$, $R^2$ and $R^3$ are all hydrogen.

3. The process of claim 1, wherein the microorganism is Streptomyces E225, NCIB 12310, or Streptomyces E225B, NCIB 12509.

4. The process of claim 3, wherein the microorganism is Streptomyces E225, NCIB 12310.

5. The process of claim 3, wherein the microorganism is Streptomyces E225B, NCIB 12509.

* * * * *